(12) United States Patent
Parfitt et al.

(10) Patent No.: US 7,458,287 B2
(45) Date of Patent: Dec. 2, 2008

(54) PARTICLE SAMPLING DEVICE

(75) Inventors: Alexander Roy Parfitt, Swindon (GB); Ian Michael Sturland, Henleaze (GB); Clyde Warsop, Lydney (GB); Paul James Dawson, Bristol (GB)

(73) Assignee: BAE System PLC, London (GB)

( * ) Notice: Subject to any disclaimer, the term of this patent is extended or adjusted under 35 U.S.C. 154(b) by 146 days.

(21) Appl. No.: 11/547,654

(22) PCT Filed: Nov. 2, 2005

(86) PCT No.: PCT/GB2005/004230

§ 371 (c)(1),
(2), (4) Date: Oct. 5, 2006

(87) PCT Pub. No.: WO2006/048641

PCT Pub. Date: May 11, 2006

(65) Prior Publication Data

US 2008/0105034 A1    May 8, 2008

(30) Foreign Application Priority Data

Nov. 5, 2004 (GB) ................ 0424658.3

(51) Int. Cl.
*G01N 15/00* (2006.01)

(52) U.S. Cl. .................................... 73/865.5

(58) Field of Classification Search ............... 73/865.5, 73/28.6, 28.06
See application file for complete search history.

(56) References Cited

U.S. PATENT DOCUMENTS

| 3,983,743 | A | 10/1976 | Olin et al. ............. 73/28.06 |
| 4,590,792 | A | 5/1986 | Chiang et al. ............. 73/28.06 |
| 6,267,016 | B1 | 7/2001 | Call et al. ............. 73/863.22 |
| 6,342,388 | B1 | 1/2002 | Van Den Wildenberg 435/287.1 |
| 2005/0274206 | A1* | 12/2005 | Coyle et al. ............. 73/864.71 |

FOREIGN PATENT DOCUMENTS

WO    WO 03/081212 A2    10/2003

\* cited by examiner

*Primary Examiner*—Hezron E. Williams
*Assistant Examiner*—Tamiko D Bellamy
(74) *Attorney, Agent, or Firm*—Buchanan Ingersoll & Rooney PC

(57) ABSTRACT

A particle sampling device is disclosed for separating and collecting particles of at least first and second mass/size ranges from an ambient fluid (e.g. gaseous) medium in which they are present, particles of the first range being of generally larger size/mass than particles of the second range. The separator is especially designed for use in an air sampling device which is designed for rapid detection of micro-organisms such as bacteria, viruses, pathogens and the like, and is designed to be portable so that it can be readily and rapidly deployed in both civilian and military environments and can be used indoors and outdoors; it can also be designed for personal use.

40 Claims, 11 Drawing Sheets

PARTICLE SAMPLING DEVICE

This invention is concerned with particle separators and collectors and is particularly concerned with devices for sampling and thus monitoring the presence of selected particles in fluids, both liquid and gases, and in particular though not exclusively for monitoring air constituents. The invention is more especially concerned with such devices that are capable of sampling ambient air to detect for the presence of chemical and biological agents present in the air.

It is perceived that there is a current and urgent need for air-sampling devices that are easy to operate, can be manufactured in large quantities, can detect and identify as many hazardous agents in the atmosphere as possible, and are highly portable so that they can be readily and easily deployed wherever and whenever required and can be highly responsive to the presence of selected particles both in the open air and inside buildings, in mass transport vehicles such as aircraft, ships, trains and buses as well as being available for personal use. It is also a requirement that such devices can identify these hazardous agents within a sufficiently short time frame that remedial action can be taken before they can have any serious effect, both in the military and non-military environments.

Previous proposals have been put forward to provide particle separation for particles as small as the sub-micron level (see for example "Particles separate doing the Tango" Biotechnology July 2004, "Continuous Particle Separation Through Deterministic Lateral Displacement" by L. R. Huang et al. Science, May 14, 2004). A further study, among others, is to be found in "Virtual Impactors: A Theoretical Study" by V. A. Marple & C. M. Chien published 1980 in Environmental Science & Technology by the American Chemical Society.

Whilst such separators are known and have been proposed for separating extremely small particles, they are not suitable as separators of sampling devices which are required for the separation and identification of microbial or bacteriological or like particles, and are not readily deployable in numbers.

The fundamental reason for this is that known particle separators are substantial, can only deal with small volumes of air or other gases in a given time frame and are primarily concerned with separation, but not necessarily with the preservation of the integrity of, the particles so separated, so that a pathogen, virus, germ or the like can be subsequently identified, due to collision of such particles as they are being separated and collected. Indeed, in the prior art, collision is identified as a definite result of the structure and operation of the separator. An example of a such a prior art proposal is that disclosed in UK patent no. 1354261 which discloses a device for collecting dust and smoke particles of micron dimensions suspended in air or other gases comprising a container with an inlet and an outlet, and a series of spaced and apertured transverse plates within the container, wherein the apertures of the first plate of the series, which is the plate that is nearer to the inlet than is any other plate which is within the container, has apertures which are so sized that the velocity of air or other gas passed therethrough is increased and which are larger than the apertures in the or each other plate which is within the container and the apertures of the or each other plate which is within the container are smaller than the apertures of the or each plate which is between that plate and the inlet so that the last plate of the series which is nearer to the outlet than is any other plate within the container has apertures which are smaller than the apertures in the or each other plate in the container, and the apertures in each plate are staggered with respect to the apertures in the adjacent plate or plates. It can be readily appreciated that such a device is of no use in collecting and analysing particles such as pathogens where the construction and arrangement of the device is such that particles will directly impact the plates and be at least damaged to the extent that identification of such pathogens would be at least very suspect.

The method of extracting air-borne particles from air or other gases using this prior art device comprises drawing a sample of the gas through a number of spaced and apertured plates in which the apertures progressively decrease in size from the first plate to the last plate and the apertures in each plate are staggered with respect to the apertures in the adjacent plates so that the gas streams change direction abruptly in progressing from one plate to another and particles suspended in the gas leave the gas streams when the velocity, together with the abruptness of change of direction, is sufficiently great and impact on the surface of the next plate clear of the holes in that plate.

Since then many collector systems have been proposed using the principle of impaction. One that demonstrates the method clearly is U.S. Pat. No. 6,463,814. This is a slit impactor, and the patent discloses one rectangular inlet, which is used to direct air onto a microscope slide. A slit impaction sampling device is for collecting airborne contaminants for subsequent analysis, includes a base with a microscope slide disposed thereon. The microscopic slide has an adhesive media located thereon to assist in adhering airborne particles on the microscopic slide. The base has a top cap secured thereto. The top cap has an inlet opening formed therethrough. The inlet opening has an outer venturi section and an inner laminar section that directs the air flow through the inlet opening into contact with the adhesive media such that the airborne particles form an impaction trace thereon. The air then flows around the microscope slide into an outlet passage and to a vacuum source.

Collision may occur in the particle stream or with walls of known separators, or both. If this occurred in separating bacteria and the like, the ability to identify that bacterium would be seriously impaired due either to damage to the bacterium, thereby potentially altering its own structure, or due to cross contamination. Consequently, known particle separators are unsuitable for use in separating and collecting particles which can be damaged by impact.

We have therefore developed a particle separator and particle collector in which the potential risk of such damage is minimised. This has been achieved by analysis of a range of bacteria, viruses etc. as to size and mass, and an understanding of the optimisation of the air flow which will permit separation of such particles without any significant collision between them.

Generally speaking, in ambient air, particles exist that are of a range of less than 50 microns. Larger particles in the atmosphere generally tend to settle and do not remain in the atmosphere. Below the 50 micron level, atmospheric particles can usually be classified into three size ranges, namely 20-50 microns, 2-20 microns and below 2 microns. Micro-organisms such as bacteria, germs, viruses and the like are normally considered to be at the lower end of the overall range, though some noxious and poisonous materials may exist in the sub 40 micron, and in particular the 2-20 micron, range. For this reason, it may also be advantageous to consider the centre range as comprising more than one 'sub-range'. For a separator of a 'universal' detector of chemical and/or biological agents, it is most important that as many pathogenic and/or toxic substances are detected as is possible, which is to say without damage thereto such as would remove the ability to identify them.

In our co-pending United Kingdom patent application no. 0420292.5, there is disclosed a separator for separating particles of first and second mass/size ranges from an ambient fluid medium in which they are present, particles of the first range being of generally larger size/mass than particles of the second range, the separator comprising a body having an inlet provided by a plurality of inlet ports through which the ambient fluid medium can be admitted into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator.

In that application, there is also disclosed a separator for separating particles of first and second mass/size ranges from an ambient gaseous medium in which they are present, particles of the first range being of generally larger size/mass than particles of the second range, the separator comprising a body having an axis and an axial inlet provided by a plurality of inlet ports through which the gaseous medium can be drawn into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator.

The present invention provides a particle collector for collecting particles of a discrete particle mass/size separated from a flow of an ambient fluid medium, the collector being particularly though not exclusively adapted for use with a separator of the type disclosed in our aforementioned UK patent application no 0420292.5. The collector comprises a chamber having mounted therein a substrate which is rotatable about an axis and onto which separated particles can be directed; the substrate having thereon a plurality of circumferentially-spaced channels each extending in a direction away from said axis and leading to a plurality of chambers in which the particles can be collected while the substrate is rotating, the collector further comprising means for depositing a fluid onto the substrate to form a film of said fluid at least in a region of the substrate onto which particles are directed during operation of the collector, the construction and arrangement of the collector being such that, as particles are deposited in the fluid, the fluid is caused to bear said particles to flow into the plurality of channels for deposition of the particles in the plurality of chambers.

Preferably the substrate comprises a rotatable wafer, which may be readily disposable. A central aperture is formed in the substrate to permit egress of the ambient fluid medium from which said particles have been separated; the region of the substrate forms an annulus around said aperture formed in the substrate.

Preferably the channels and the chambers are formed radially outwardly of the region, and may be arranged radially of the axis of rotation of the substrate. The channels and chambers may be provided by a layer of material which is bonded to the substrate.

Preferably the means for depositing a fluid onto the substrate comprises a plurality of spray nozzles arranged above the substrate. Ideally, the fluid deposited onto the substrate is purified water or a saline solution. A reservoir may be provided for storing a quantity of fluid for deposition onto the substrate; means is then preferably provided for recycling said quantity of fluid.

A fan may be employed for causing the flow of the ambient fluid medium to enable said particles and said ambient fluid medium to be drawn into the collector. Alternatively, micropumps may be used.

Sensor means may be provided adjacent each chamber for sensing the presence of a particle of any selected specie. Means can also be provided for recording parameters associated with any selected particle that is sensed by any sensor means.

In one embodiment of a collector according to the present invention, the chamber has a ceiling and the means for depositing fluid onto the substrate is mounted in or on the ceiling above said region of the substrate, the ceiling further providing apertures for permitting ingress of said particles into the chamber.

In a further embodiment of the present invention, a particle collector may comprise a second chamber having mounted therein a second substrate which is rotatable about said axis, the second chamber being located beneath said, first, chamber with access between the first and second chambers being provided whereby any particles uncollected in the first chamber can pass into the second chamber for collection on the second substrate, the second substrate having thereon a plurality of circumferentially-spaced channels each extending in a direction away from said axis and leading to a plurality of chambers in which the particles can be collected while the first and second substrates are rotating, the second chamber being provided with second means for depositing fluid onto the second substrate to form a film of said fluid at least in a region of the second substrate onto which particles are directed during operation of the collector.

The present invention also provides a particle separator/collector for separating particles of a discrete particle size/mass from a flow of an ambient fluid medium, such as ambient air, and for collecting the separated particles, the separator/collector comprising a plurality of superimposed chambers each having mounted therein a substrate which is rotatable about an axis and onto which particles can be directed from the flow of ambient fluid medium, each substrate having thereon a plurality of circumferentially-spaced channels each extending in a direction away from said axis and leading to a plurality of chambers in which the particles can be collected while the substrate is rotating, the collector further comprising means for depositing a liquid onto each substrate to form a film of said liquid at least in a region of the substrate onto which particles are directed during operation of the separator/collector, the construction and arrangement of the separator/collector being such that, as particles are deposited in the liquid, the liquid is caused to bear said particles to flow into the plurality of channels for deposition of the particles in the plurality of chambers, and means for causing the ambient fluid medium to flow through the plurality of chambers to exhaust.

The present invention further provides, in another aspect, a particle collecting and sampling device comprising a separator for separating particles of first and second mass/size ranges from an ambient fluid medium in which they are present, particles of the first range being of generally larger size/mass than particles of the second range, the separator comprising a body having an inlet provided by a plurality of inlet ports through which the ambient fluid medium can be admitted into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator; a particle collector of the type disclosed and claimed in our aforesaid UK patent application no. 0420292.5; and means for propelling air through the separator to the collector for collection thereby.

The present invention further provides, in yet another aspect of the present invention, a particle collecting and sampling device comprising a separator for separating particles of first and second mass/size ranges from an ambient gaseous medium in which they are present, particles of the first range being of generally larger size/mass than particles of the second range, the separator comprising a body having an axis and an axial inlet provided by a plurality of inlet ports through which the gaseous medium can be drawn into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator; a particle collector of the type disclosed and claimed in our aforesaid UK patent application no. 0420292.5; and means for propelling air through the separator to the collector for collection thereby. A preferred sampling device, including such a separator and collector, is designed to be portable and to accommodate a flow rate of air through the sampling device of approximately 200 liters/min., this being considered as adequate to sample ambient air both in a battlefield environment and in the civilian environment.

To effect this air flow, the sampling device, which is ideally of but not limited to a cylindrical shape, is of a diameter of approximately 100 mm, and so can be readily held in the hand. It will be readily understood that a separator of a device according to the present invention can be constructed so as to be of any convenient shape and size and that it need not be of cylindrical shape.

In a separator of the preferred embodiment of separating and collecting device described hereinafter with reference to the accompanying drawings, the ports of the plurality of inlet ports of the separator are generally of substantially similar size and shape and are arranged concentrically around the axis. It will be readily appreciated that, although in the illustrated embodiment, the inlet ports are so arranged and sized, this is predominantly a design consideration and therefore the ports can be arranged otherwise and their respective sizes, dimensions (i.e. cross-sections, length etc.) and positions relative to one another can be varied according to requirements regarding the size and/or mass of particles to be collected.

Preferably, each chamber has an axis parallel to the axis of the container and the outlet ports around the periphery of each chamber are arranged in concentric arrays about the respective chamber axis; the concentric arrays of outlet ports are preferably arranged in an annular gallery above a floor area of the respective chamber.

Each of the outlet ports may be provided by a passageway leading to an annular space formed beneath the gallery, the annular space being isolated from the chamber. One or more ducts leads from the annular space and is/are arranged for alignment and connection with a particle collector when the separator is connected thereto.

A second annular space is, in a preferred embodiment of device according to the invention, provided beneath said annular space, and said second annular space is then connected to said annular space whereby particles can pass from said annular space to said second annular space, said second annular space having outlets therefrom whereby said particles can be directed to said particle collector when the separator is connected thereto.

The particles of said second range will preferably include particles of discrete third and fourth size/mass ranges where particles of the third range are of greater size/mass than the fourth range, the separator being capable of extracting particles of the fourth range in said annular space and particles of the third range proceeding to the second annular space.

In a further embodiment of a separator of a device according to the invention, a plurality of annular spaces may be provided beneath said second annular space, each annular space of said plurality thereof being then connected to an immediately upper annular space whereby particles can pass from said immediately upper annular space thereto, and each annular space having outlets therefrom whereby said particles can be directed to said particle collector when the separator is connected thereto. Each of the inlet ports has a floor and a lowermost one of said plurality of annular spaces will then be connected with an aperture leading to an outlet beneath said floor.

Particles of the fourth range can be separated from particles of the third range is provided by separating said annular space into a first annular space and a second annular space with a partition therebetween such that the second annular space is separated from the outlet ports by the first annular space, the first annular space having an exit which is transverse to the axis of the respective chamber and through which particles of the fourth range can be drawn for collection, while the particles of the third range are directed through further outlets for separate collection.

Such a device is ideally portable and may be wall-mountable. It also may include means for drawing air through the separator. Such means is preferably a battery driven fan though where proposed to be used in a fixed installation (e.g. one in which it will be used to monitor air content on a long term basis), it may be connected to a power source such as a mains source of electricity. A sampling device according to the present invention may also be adapted for use by an individual wearer such as military personnel, medical personnel or security personnel and for such purpose can be fitted with a clip or the like whereby it can attached to a belt.

The present invention further provides a method of making a device according to the invention which comprises fabricating the separator and collector from a plurality of wafers which are laminated together. Alternatively, a separator/collector of a device according to the invention could be manufactured from suitable plastics material by, for example, laser drilling.

Additional features of the invention will become apparent from the following description of embodiments of the invention which are illustrated by way of example in the accompany drawings, in which:

FIG. 1 is a perspective view of an air sampling device which includes a particle separator of a device according to the invention;

FIG. 2 is a more detailed perspective view of the separator shown in FIG. 1;

FIG. 3 is a partially cutaway perspective view of the upper section of the separator;

FIG. 4 is a plan view of an upper section of the separator shown in FIG. 2;

FIG. 5 is a more detailed perspective view of the upper section of the separator;

Figure 1:
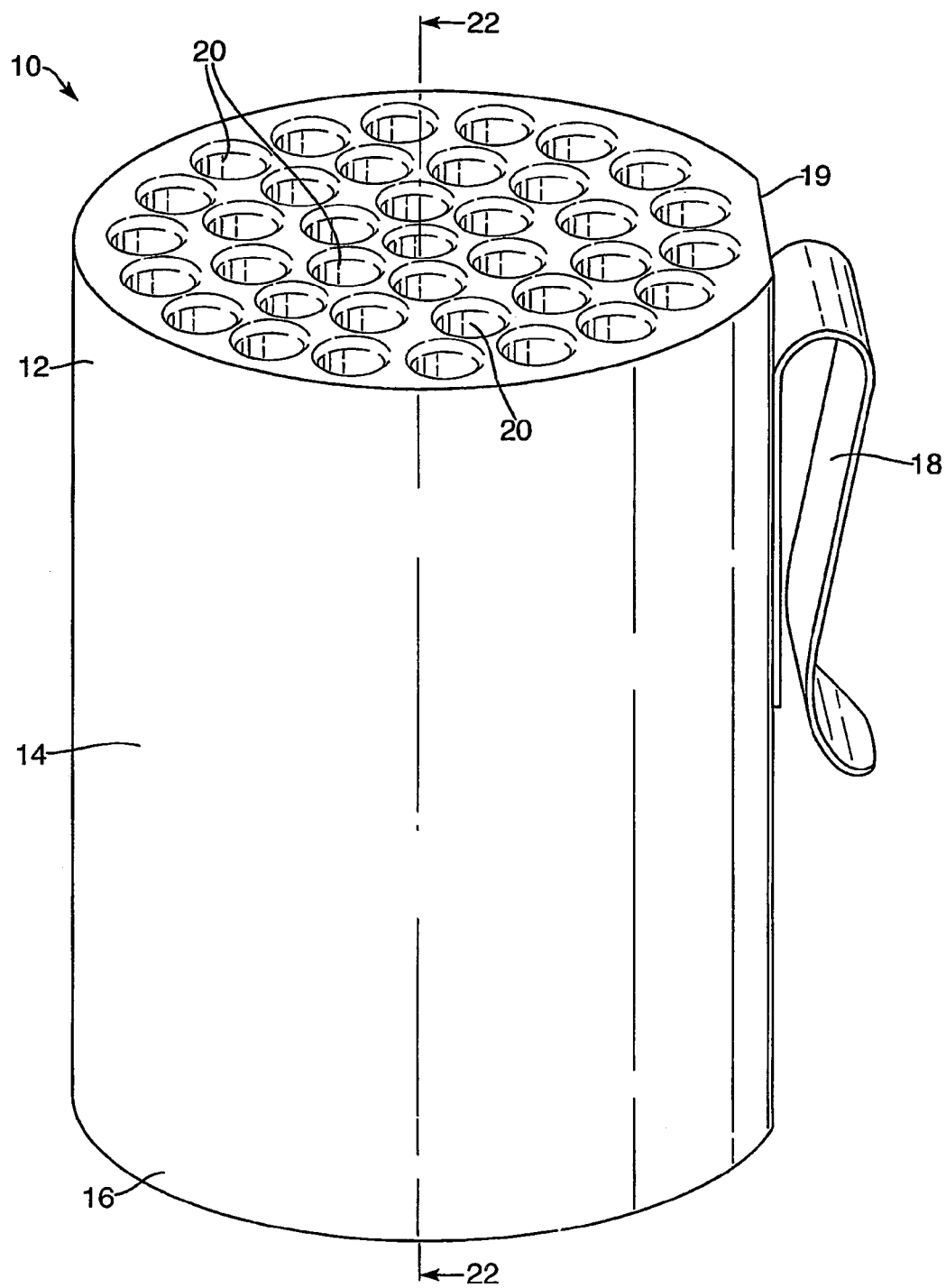

Referring firstly to FIG. 1, there is shown therein a portable air-sampling device 10, which incorporates a particle separator 12, according to the present invention. The device 10 is substantially cylindrical (though, as previously mentioned, this is not essential) and comprises the separator 12 providing an upper section of the device 10, a second or central section 14 in which are provided means for operating the device and for collecting and analysing the collected particles from the surrounding atmosphere, and a third or base section 16 in which a fan is mounted for drawing air through the device 10 when it is operated. Though of substantially cylindrical shape, the illustrated device has a flat 19 and the central section 14 has a clip 18 secured to the flat whereby the device can be attached to a wearer's belt or clothing or by which it can be mounted on a wall or other appropriate fixing, The separator 12 is intended, as discussed above, for use in separating particles from the atmosphere into the three cited size ranges, which, at the particle types and sizes under consideration, equates closely to the respective mass ranges of those particles. It will be clearly understood that, though the illustrated embodiment is hereinafter described with respect to particle size, the invention is equally useful in separating particles by reference to their mass or by reference to both mass and size.

Figure 2:
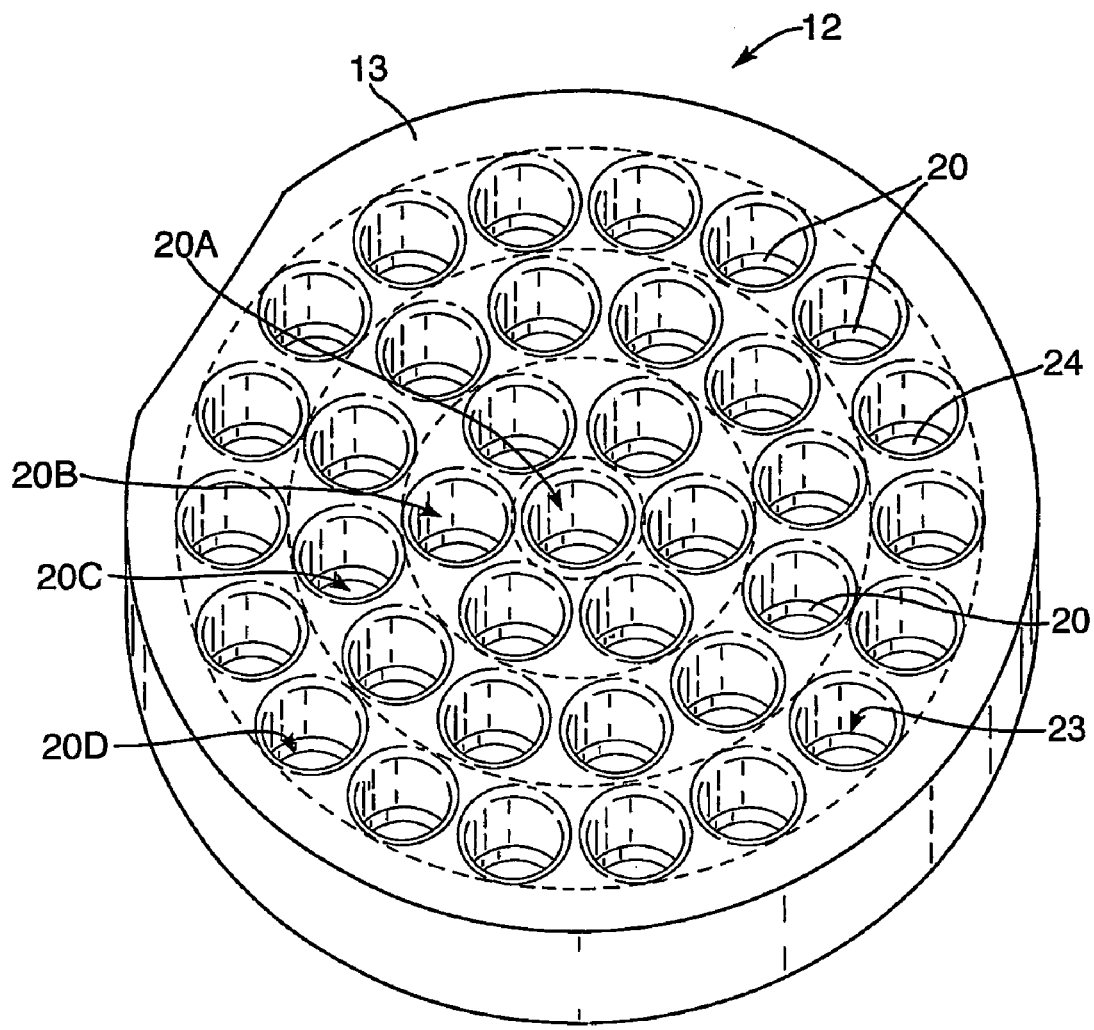
Figure 3:
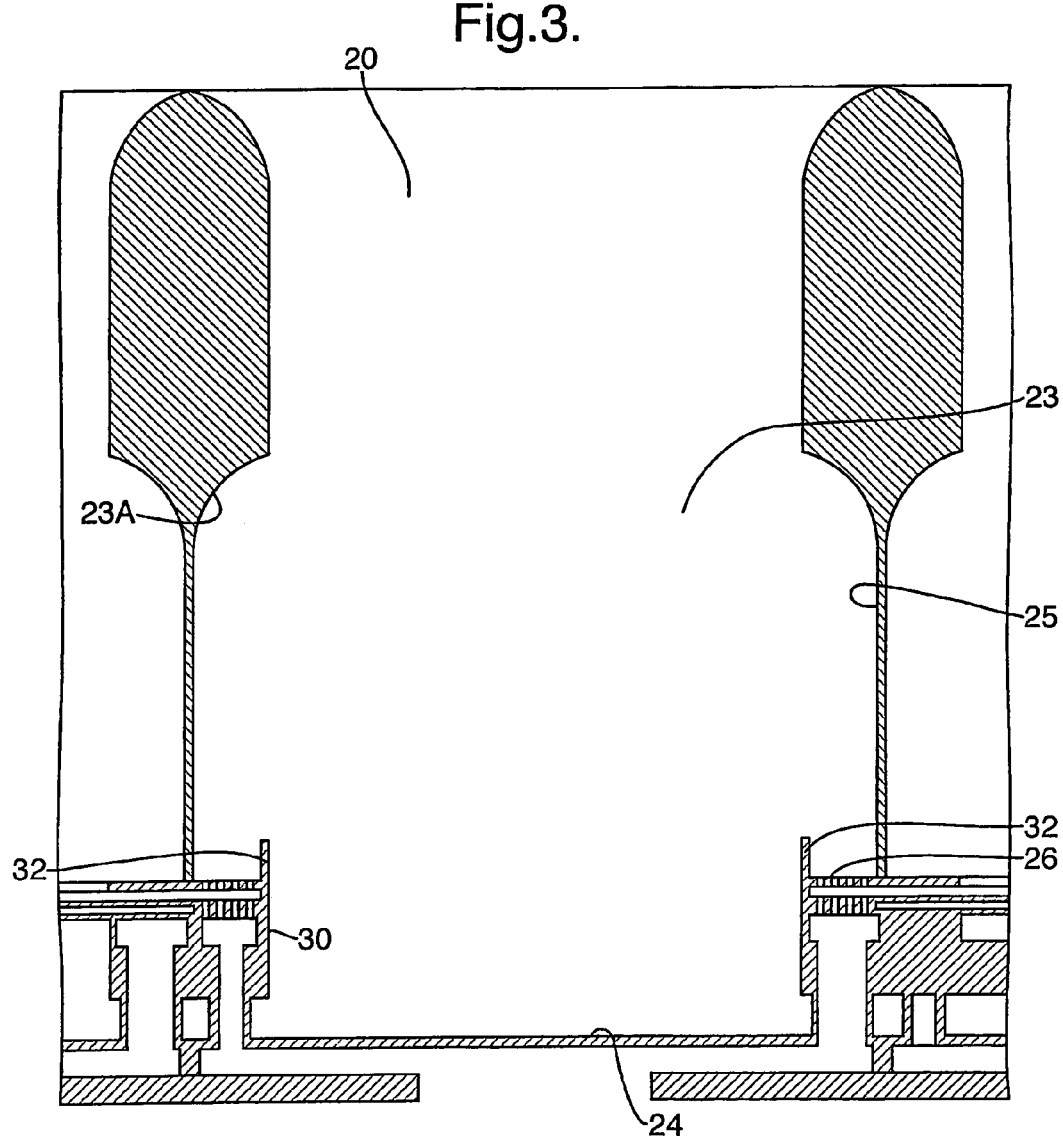
Figure 8:
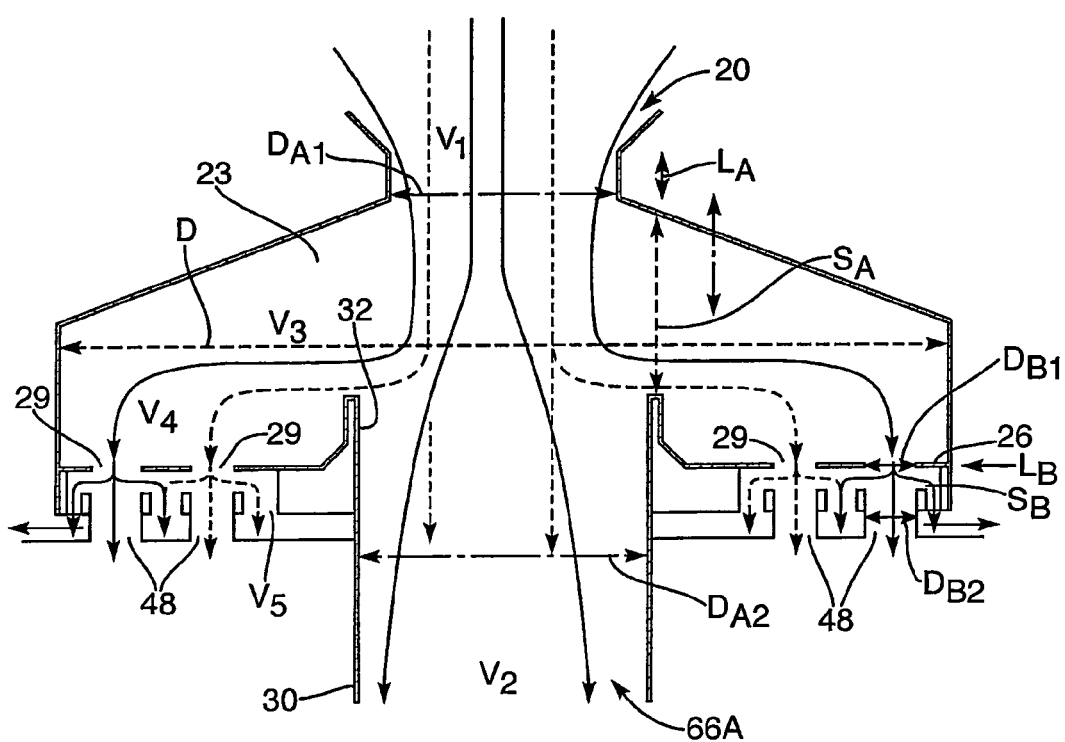
FIG. 8 is a schematic diagram showing air flow through the separator.
Figure 9:
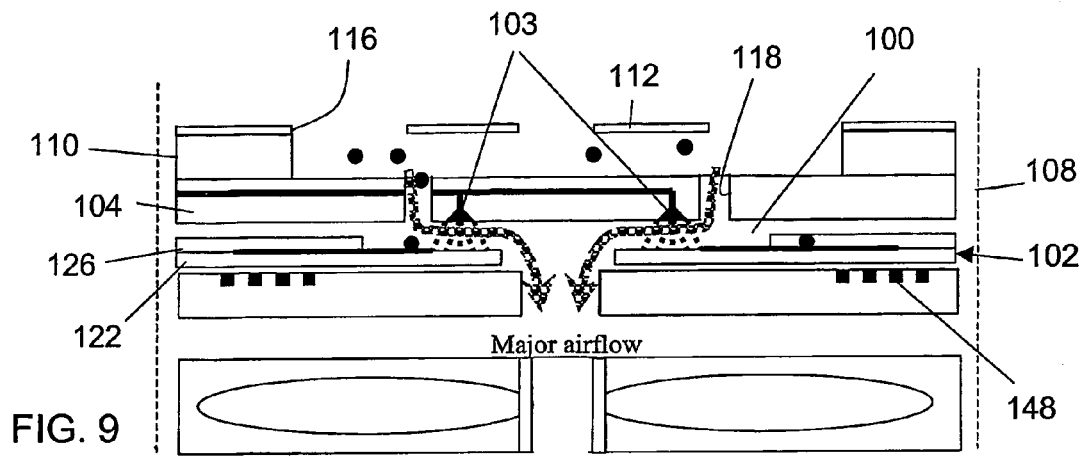
FIG. 9 is a schematic cross-sectional view of a particle collector according to the present invention for a device according to the invention.

Referring to FIG. 2, the separator 12 of the illustrated embodiment is in the form of a body 13 which has a plurality of inlet ports 20. In the illustrated embodiment, there are thirty-seven. The device, and therefore the separator has a general axis 22, (shown in FIG. 1 but not FIG. 2), and the ports are arranged around a central port 20A (FIG. 2) in three concentric arrangements 20B, 20C and 20D, with six ports in the innermost circle 20B, twelve ports in the intermediate circle 20C, and eighteen ports in the outermost circle 20D. In FIG. 2, these concentric arrangements of the ports are indicated by dotted lines. (In alternative embodiments of the invention, it is not necessary that the ports be so arranged. It is important though that the arrangement of the ports optimises the ability of the plurality of ports to take in the airflow that is desired.) Each port is of substantially cylindrical shape but tapering very slightly with the depth of the port and is formed as a recess in the body 13 of the separator, with its cylinder axis (not shown) parallel to the axis 22 (shown in FIG. 1). Referring also to FIG. 8, which is a diagrammatic representation of the construction and arrangement of the separator and approximates to FIG. 4, it will be seen that each port 20 has a depth $L_A$ and a diameter $D_{A1}$ at its lower extremity and leads to a chamber 23 which is of a larger diameter D than the port 20. As shown in FIG. 3, chamber 3 has an annular open roof 23A FIG. 3) which has the shape of a frustum of a sphere descending to a substantially cylindrical wall 25. The chamber 23 has a floor 24 and above the floor is formed a gallery 26 provided by an annular plate-like structure 28 in which are formed five concentric circles of outlet ports 29 (shown in FIG. 4). In the illustrated embodiment, there are of the order of six hundred and fifty-seven such outlet ports in each structure 28. Thus, the thirty-seven inlet ports provide a total of some 24,309 outlet ports 29, each having a diameter $D_{B1}$ and a depth $L_B$ (see FIG. 8). It will be appreciated that the exact number of these ports and their size and depth will be dependent upon the size or mass of particle(s) to be separated at this and subsequent stages of the separator and the velocity of the particles being drawn into the separator.

In a portable device as shown in FIG. 1, designed for separating particles of a size not exceeding about 20 microns from ambient air, and for subsequently separating those particles into sub-groups, the external diameter of the device is approximately 100 mm, and the internal diameter $D_{A1}$ of each inlet port 20 is 10.27 mm while the internal diameter $D_{B1}$ of each outlet port 29 is 183 µm. We have determined that with such dimensions, it is possible to induce a flow rate of about 185 to 200 liters per minute through the device under the desired conditions as discussed below.

As shown in FIG. 3, radially outwardly, the gallery 26 is bounded by the annular wall 25 defining the periphery of the chamber 23, while radially inwardly, the gallery is bounded by a continuous curtain wall 30 which descends from the plane of the gallery 26 and terminates at a height above the floor 24 which is approximately one-third of the vertical separation of the gallery 26 from the floor 24. At the top of the curtain wall, an upwardly-projecting rim 32 is provided.

Figure 6:
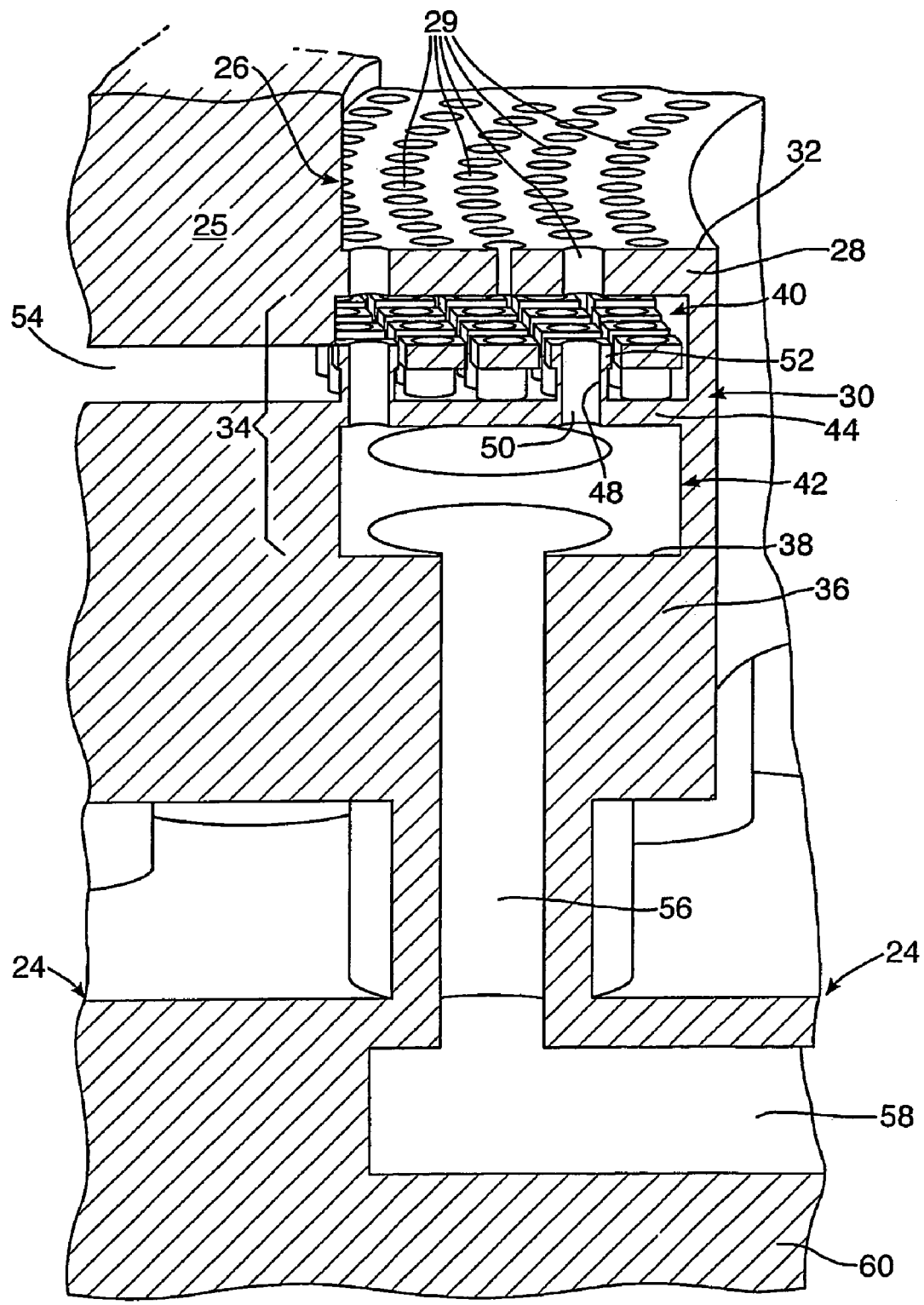
FIG. 6 is a cut-away part-sectional view of the separator.

Referring to FIG. 6, behind the curtain wall (i.e. radially outwardly of the curtain wall) and beneath the gallery 26, an annular space 34 is formed which is isolated from the chamber 23 by the curtain wall, the annular space 34 having an annular base 36 which is integral with the outer body 13 of the device 10. The upper surface 38 of the annular base 36 is located approximately midway between the top and bottom of the curtain wall 30 and is of a thickness such that it extends to the bottom of the curtain wall.

The annular space 34 between the gallery 26 and the surface 38 is separated into a first, upper, annular space 40 and a second, lower, annular space 42 by an annular intermediate floor 44. This annular floor provides a partition between the two annular spaces 40 and 42 and has a plurality of further outlets 48 provided by apertures 50 formed in the annular floor 44, the apertures each having upward chimney-like extensions 52 each of which has an internal diameter $D_{B2}$ (see FIG. 8) and is spaced from the underside of the gallery 26 by a distance $S_B$. There are as many apertures 50 and associated extensions 52 as there are outlets 29, the apertures 50/extensions 52 being axially aligned with the outlets 29.

Figure 4:
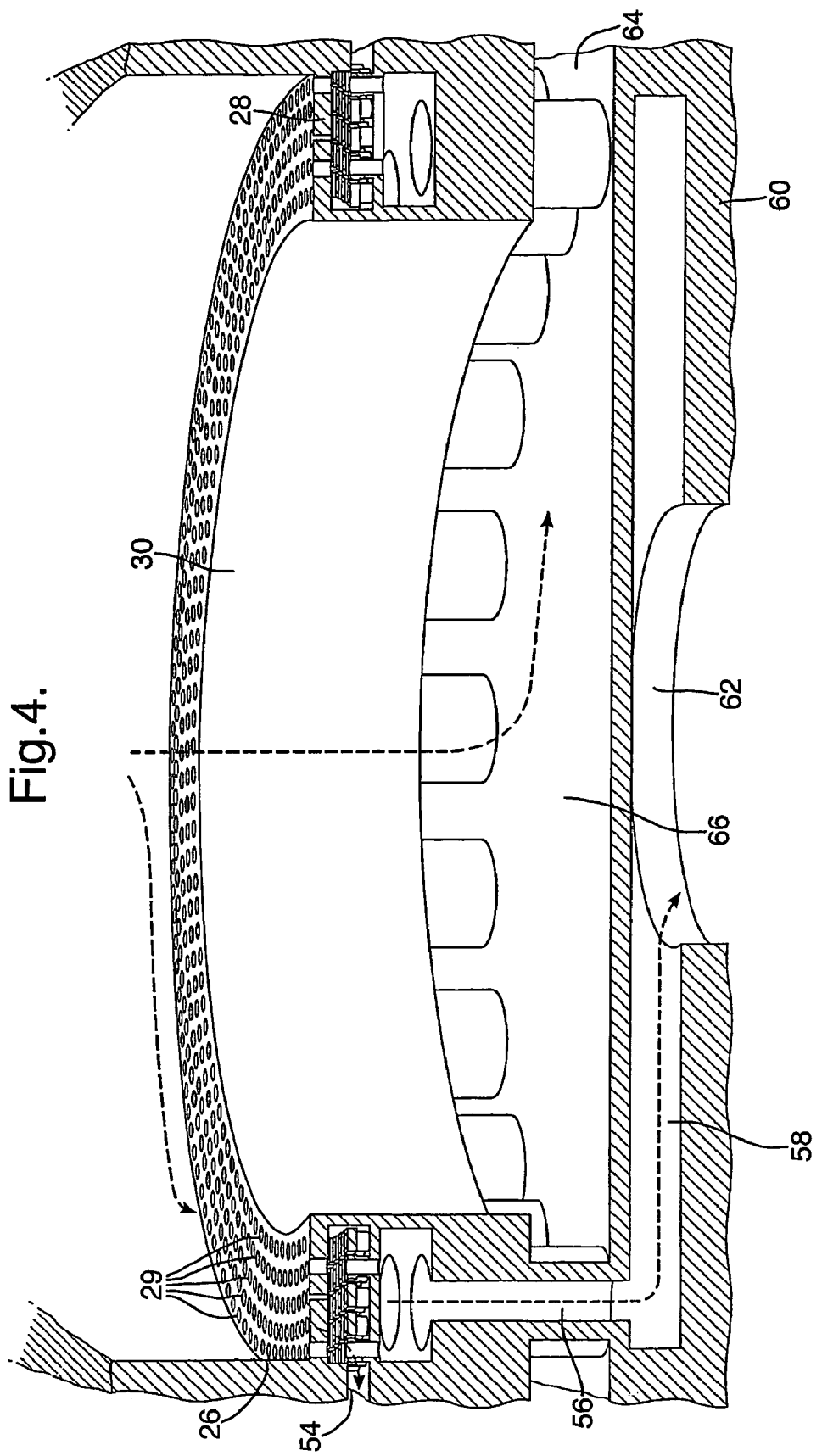
Figure 5:
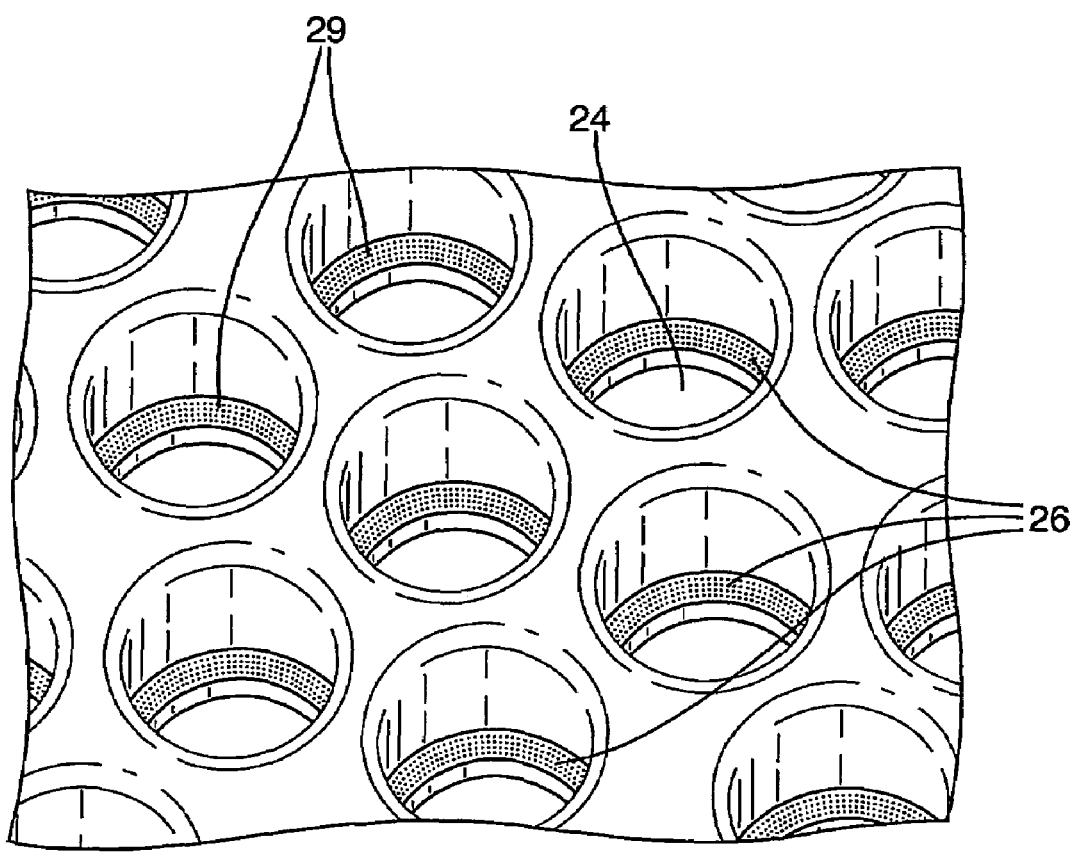

Extending radially outwardly from the first annular space 40 is a plurality of ducts 54 (FIGS. 4 and 6), only one of which is shown in FIG. 6. These ducts, as explained below, lead to a particle collector which is provided in the control section 14 of the device 10. Extending downwardly from the annular upper surface 38 of the annular base 36, and through the base is a plurality of cylindrical shafts 56 having axes parallel to the axis 22. These shafts connect with a shallow, cylindrical space 58 which is formed between the underside of the floor 24 and an underfloor 60 which has a central aperture 62 formed therein. As shown in FIG. 4, this central aperture 62 which is one of thirty-seven such apertures, leads to the aforementioned particle collector.

Figure 7:
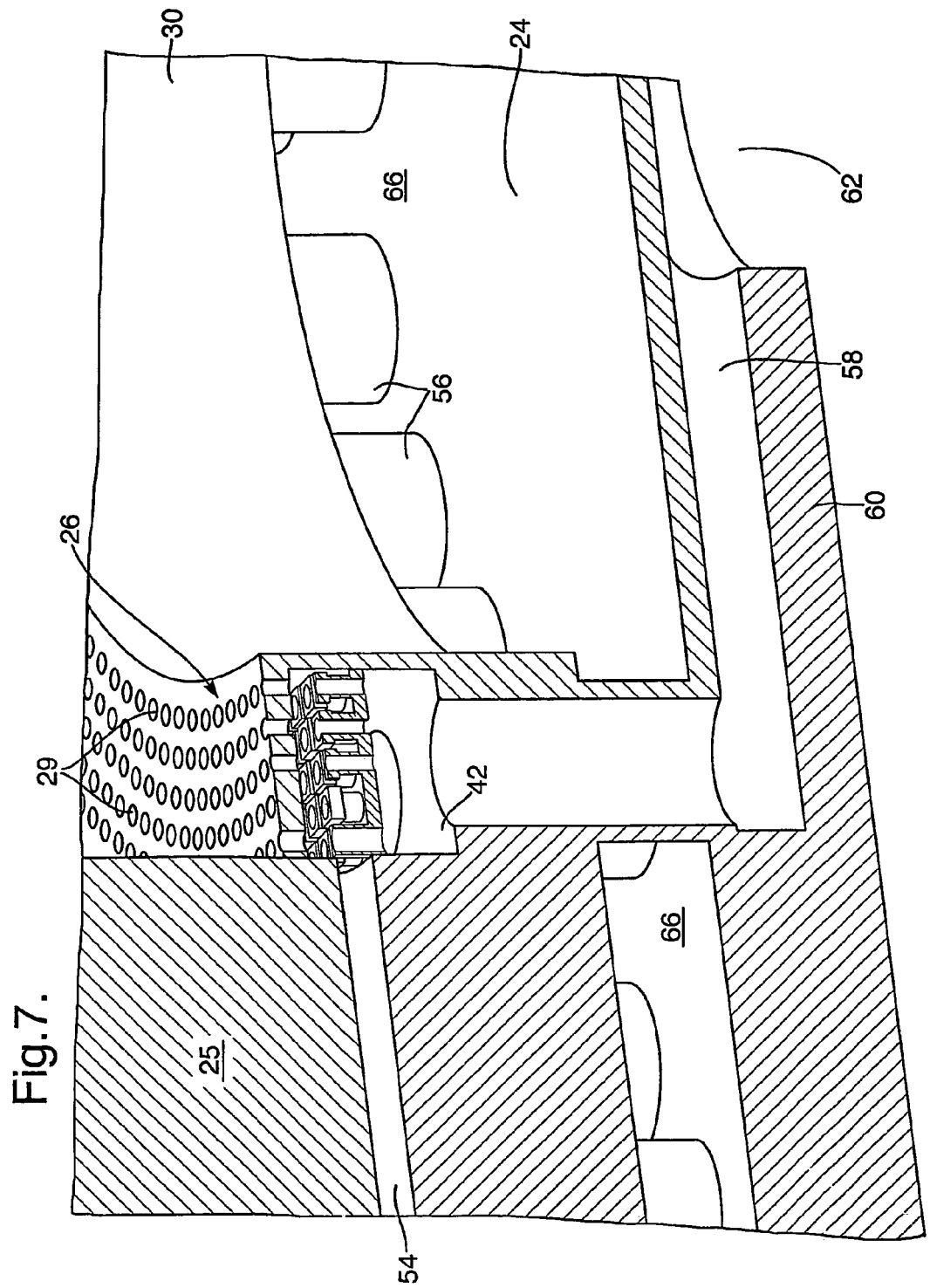
FIG. 7 is a close-up cut-away part sectional view of the separator.

The lower part of the chamber 23 is bounded by an annular colonnade 64 of the shafts 56 (FIGS. 4, 6 and 7), defining gaps 66 between adjacent columns. The spacing defining the gaps 66 extends through to similar spacing beneath each of the thirty-seven inlet ports 20, thereby providing a unitary space which, though not shown, can be coupled to exhaust or to the particle collector of the device, as required.

The function and operation of the separator is as follows:

Inertial mass is used to separate a single stream of particles into two streams depending upon their weight. Large particles will continue in a forward direction whilst smaller, lighter particles are drawn off to the side. The principle of this is shown in FIG. 8.

Air is drawn into and through the device by operation of suction means which in the present embodiment of the invention is a battery-operated fan mounted in the base section 16 of the device. The fan is able to draw air into the device via ducts (not shown) leading to the fan from the particle separator and which may or may not bypass the particle collector mounted in the central section 14 of the device. The manner in which air is drawn through the central and base sections of the device is not central to the present invention and will not therefore be further described.

Of course, the particle collector itself is connected with the radial ducts 54 and with the central aperture 62, and so air is drawn through them as from the colonnaded spacing 66 between the shafts 56.

Air enters the device 10 through the ports 20, and as shown schematically in FIG. 8. The air is drawn down through the outlets 29 and through the space 66. Air passing into the space 66 can be drawn off to exhaust. On the other hand, air passing through the outlets 29 enters the first annular space 40 below the gallery 26 and, depending upon particle size, is either drawn off through the radial ducts 54 or passes through the extensions 52 into the second annular space 42 beneath the intermediate floor structures 44, from where it is drawn into the central aperture 62. Air drawn through the ducts 54 and the aperture 62 is conducted to the particle collector.

The design, geometry and proportions of the separator are calculated such that only particles of given size ranges are collected. Thus, for example, with the illustrated embodiment, particles of a size, of say less than 20 microns, and which are drawn into the separator with a given inertia, which is dependent partly on the speed of the fan, are more readily influenced by the suction effect of the fan than larger sized particles, which proceed under their own momentum, as shown in FIG. 8. If the separator was designed to separate particles according to their mass only, then similar considerations would apply.

The suction effect of the fan is exerted through the outlets 29 and through the space 66. This is represented schematically in FIG. 8 by the passages 29 and the vertical passage 66A. As can be seen from FIG. 8, heavier particles, in the upper range of particle size/mass, continue to flow in approximately the same direction as they enter the separator while lighter particles, in the lighter size/mass range, are drawn off through the passages 29. Some particles at the upper end of the lighter mass range may continue along the passage 66A but the much larger proportion will be drawn into the passages 29. Provided that sufficient quantities of such particles are drawn off into the passages to permit the collector to detect their presence and allow identification, the precise quantity of particles is not important.

The lighter particles can then, in a subsequent separation, themselves be further separated into sub-ranges in one or more further separation stages.

The separation of the particles is determined initially by the internal diameter $D_{A1}$ of each of the inlet ports 20, which, for the particle separation with which the present invention is primarily concerned, we have determined should be a maximum of 12 mm at its entrance, tapering to a minimum diameter of 10.27 mm. With these magnitudes, we have determined that 95% of the airflow will continue in the major flow and be channeled into the particle separator for subsequent separation and analysis.

The depth $L_A$ (FIG. 8) of the inlet ports together with the overall total area of the outlets (each it will be remembered is of diameter $D_{B1}$) represented by the passages 29 is also determinative in assuring that the flow of air is as desired. It will be readily appreciated that the airflow as represented will be similar for each outlet 29, though this is not necessarily always so and depends upon the types and nature of particles to be separated. At the inner edge of the gallery 26 is a perimetral rim or wall 32 (shown in FIG. 3 and in exaggerated form in FIG. 8 but omitted from the remaining Figures for the purposes of clarity only) which is of a height such that the vertical separation $S_A$ of the wall 32 from the roof 23A permits particles of the correct size (i.e. the range(s) of sizes of interest) to be entrained to enter the outlet ports 29. Without the provision of the wall 32, it is possible that particles could collide with the upper edge of the curtain wall 30 and be adversely affected and yet still be entrained to flow into the outlets 29. Provision of the wall 32 prevents this from occurring.

The dimension $D_{A2}$, which represents the cross-sectional area through which air which is not to be analysed is allowed to vent to atmosphere, is such as to allow its unrestricted dispersion.

Particles are drawn into the separator 10 at a velocity $V_1$ and as they enter the larger volume of the chamber 23, those particles which descend to the floor of the chamber acquire a velocity $V_2$ while those which veer towards the outlet ports 29 acquire a velocity $V_3$. As the latter particles enter the outlet ports 29, the velocity changes to a velocity $V_4$ and those particles that pass through the apertures 50 and the extensions 52 maintain this velocity while those which are diverted into the upper space 40 acquire a velocity $V_5$.

Fabrication of the separator is essentially by forming elements of the separator from a sequence of wafers made from inert material such as silicon dioxide and assembling the wafers in the appropriate sequence.

It will be clearly understood from the foregoing description that although the invention has been described with reference to a separator having provision for separation of airborne particles into three size/mass ranges, the invention can be readily developed to provide for separation of more than three ranges by increasing the number of separation points. For example, by appropriate changes to the geometry of the outlets shown in FIG. 6 and addition of one or more levels corresponding to the annular spaces 40 and 42 (with their appropriate inlets and outlets), it will be possible to effect separation of airborne particles into a significantly larger number of separation stages while, with the method of fabrication used, retaining the portable characteristics of the sampling device of which it will form a part. In addition, with the correct geometries, a separator according to the present invention can be readily adapted to separate liquids and particles present in liquids.

Furthermore, depending upon the environment and conditions in which a separator, as part of a sampling and detection device, might be used, the device itself may be enclosed within a protective container.

Referring now to FIGS. 9 to 12 these Figures illustrate diagrammatically a particle collector according to the present invention which is mounted at the lower part of the central section 14 of the device shown in FIG. 1.

The illustrated particle collector comprises a chamber 100 in which is mounted a substrate 102 which is rotatable about an axis which is collinear with the axis 22 shown in FIG. 1 and onto which separated particles from the particle separator section 12 can be directed, as hereinafter described.

Figure 12:
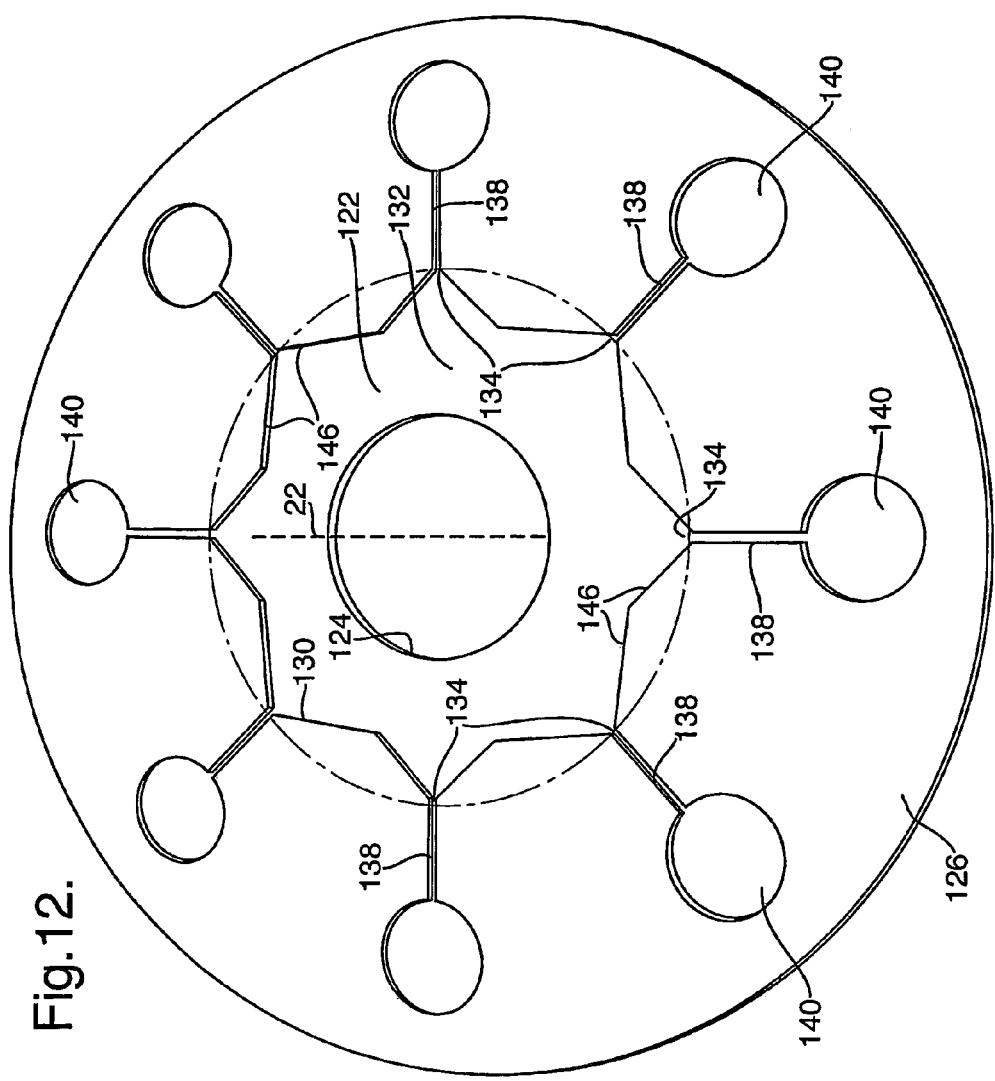
FIG. 12 is a perspective view of a disc of a particle collector according to the present invention.

The device further comprises a fan 101 which is mounted below the substrate 102 and is electrically driven from a power supply 105 and particles and air are drawn through the device by the fan during its operation. The rate at which the fan 101 operates is calculated to ensure that particles are drawn into the device for collection without any significant collision with themselves or with the structure of the device, until they reach the substrate. The substrate 102 can be driven from the same power supply as the fan or from a separate power supply as desired.

The illustrated device is shown having a power supply provided by batteries 107 mounted in the base of the device.

Where the device is intended for personal use and is designed to be carried on the person, then a single power supply can be used, installed in the device itself, but where the device is installed in numbers, as for example, in locations where the public at large are likely to be present, then the device can be operated in concert with similar devices at the same location from one or more local and general power supplies.

The collector also comprises means for depositing a fluid, which may be purified water or a saline solution, onto the substrate to form a film of fluid. The means may be any spray means in the form of nozzles capable of depositing a fine mist or spray of fluid onto the substrate and are generally indicated at 103. The fluid is drawn from a replenishable source or reservoir (not shown) mounted within the device, via conduits 109 which are formed within the partition 104, and can be recycled as hereinafter described once it has served its function of carrying particles as also hereinafter described.

Where desired or appropriate, the fluid, typically water or saline solution as mentioned above, may contain a proportion of an inert thickening agent such as glycerine, depending upon the type of particle that is to be collected by the device. Preferably, the thickening agent will be added to the fluid in the reservoir but may be admixed with the fluid while the latter is en route to the spray 103. The deposited fluid, shown in FIGS. 9, 10 and 11, provides a film of fluid which, we have found by experiment can be of the order of 5 microns thickness where it is desired to collect particles of a size in the range of 2-20 microns with a rate of rotation of about 500 rpm. The film thickness may of course be varied, but is largely dependent upon the viscosity of the fluid itself, the rate of rotation of the substrate and the size of the particles to be collected. We have found that with a rotation rate of significantly less than 500 rpm, say at approximately 200-300 rpm, the film does not develop evenly at the lower end of the range, while at the upper end, ripples are produced in the film, leading to uneven movement of particles.

The chamber 100 is defined by an overhead partition or ceiling 104 and a base section 106 and side walls 108 of the container within which the sampling device is installed. Spaced above the partition 104 by an annular spacer 110 is a planar cover 112 which is of generally circular shape and defines a plenum 114 between it and the partition 104, in which plenum, particles and the accompanying airflow emanating from the cylindrical spaces 58 beneath the floors 24 of the thirty-seven inlet ports 20 shown in FIGS. 1, 2 and 5, via the central apertures 62, can be combined and passed to the collector.

The planar cover 112 corresponds to the underfloor 60 shown in FIG. 4 and is provided with the apertures 62 through which particles that have been separated in the separator can pass through into the plenum 114, where they and the accompanying air can circulate as it flows though the collector.

The partition 104 is also provided with a plurality of apertures 118 which are of a diameter such as to permit flow through the collector without collision with the partition. In the illustrative device, these apertures are arranged in a concentric ring around the axis 22 of the device, and there will be of the order of fifty such apertures. The arrangement is such that as air is drawn through the device, the particles are drawn through the apertures 118 with the accompanying air and the rate of flow is controlled such the lighter air molecules will be drawn radially to the centre of the chamber where they exit through a central exit aperture 120 formed in the base section 106. The particles of interest however, being of greater size/mass, will impinge on the fluid on the substrate 102.

The substrate 102 is formed of a wafer or disc 122 which can conveniently be manufactured from silicon dioxide. The disc has a central aperture 124 aligned with the aperture 120 formed in the base section 106 and through which air can be drawn to exit from the device.

The substrate 102 is formed as a laminate of the wafer 122 and a second wafer 126 which is shaped as shown in FIG. 12 (a third wafer 128, which is also shaped as described below, may be positioned on the second wafer). Shaping of the wafers can be by any conventional means, including by etching.

The wafer 122 is a circular disc having the central, circular, aperture 124 formed therein.

The wafer 126 is formed with a central eight-pointed-star-shaped aperture 130 which is of larger dimensions than the central aperture 124 of the wafer 122, such that when the two wafers are bonded together, a central annular, but externally star-shaped, area or region 132 of the wafer 122, which will be underlying the wafer 126, is exposed.

At each of the eight apices of the star-shaped aperture 130, channels 138 are formed, as by etching. In the wafer, these channels extending radially from the axis 22 and terminating in collection chambers 140. The purpose of these channels 138 and of the chambers 140 is described below but it will be appreciated that the channels may be formed other than radially.

The third wafer, if required, is annular in shape and is placed on the wafer 126, thereby sandwiching the latter between it and the wafer 122. The wafers may be bonded together by any suitable bonding agent. However, we have found that by forming the wafers with very flat surfaces, Van der Waals forces are sufficient to bond the wafers together if the wafer laminate is maintained for the requisite period of time. The circular aperture in the third wafer is of larger diameter than that of the wafer 122, the diameter corresponding to the largest dimension of the star-shaped aperture 130 of the wafer 126, as indicated by the chain-dotted line 142 in FIG. 12. If desired, the aperture may be of larger or smaller diameter than indicated in FIG. 12.

Each of the channels 138 is preferably of a width in the range 20-200 microns, the width of the channel being determined by the mass/size of particle to be collected and by other factors such as the rate of flow and viscosity of the fluid used and the speed of rotation of the disc in operation. In FIG. 12, eight such channels are shown. However it is foreseen that many more than eight may be provided, depending upon the number of particle types that it is desired to collect and detect. For example, each chamber may be served by more than one channel.

The dimensions of the chambers 140 can also be varied, the principal, but not the only, criteria in determining size and shape being the rate at which particles are desired to be collected and the flow of fluid into those chambers. In FIG. 12, the chambers 140 are shown as being circular but other shapes are foreseen, including those with an elliptical or triangular or diamond shaped profile. It is also possible to vary the number of chambers that are used for collecting particles.

When the device is operating to draw particle-containing air into and through the device and the collector is being operated by rotation of the substrate 102, the rate of rotation of the substrate will be dependent upon the types of particles that are to be collected for identification and the rate at which it is necessary to process those particles through the device.

Figure 10:
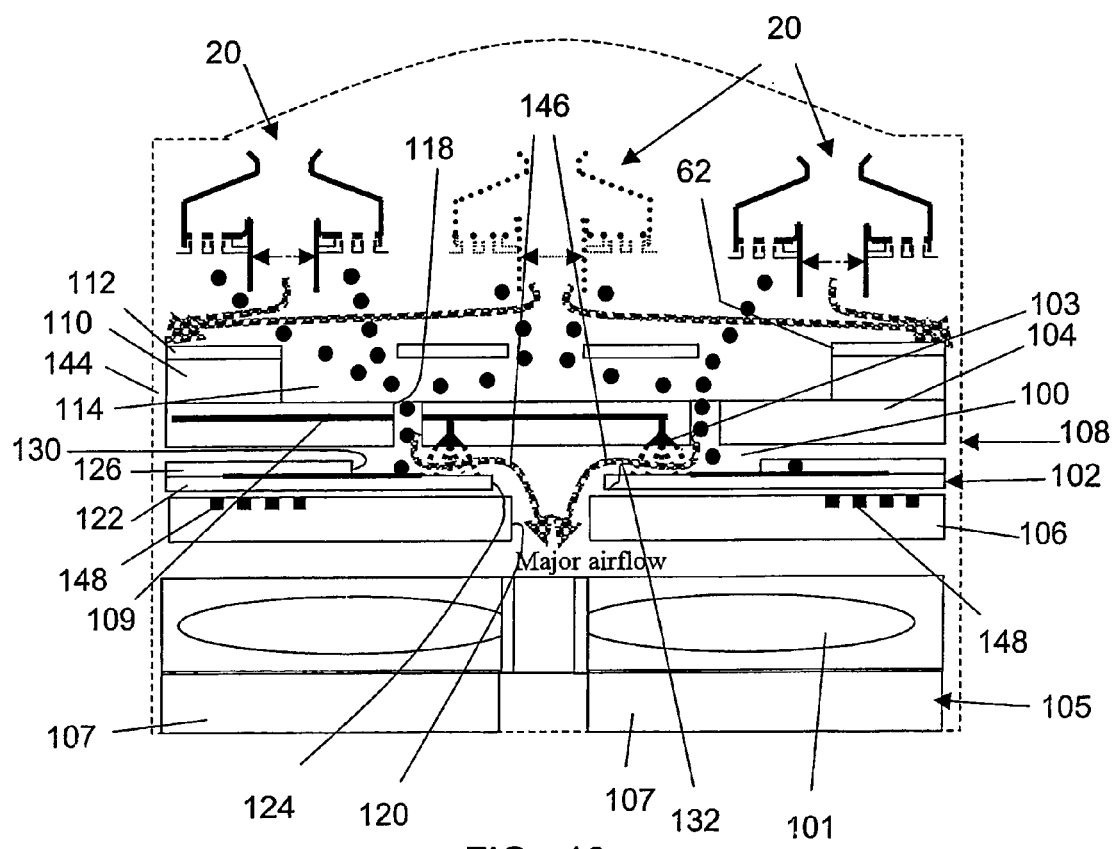
FIG. 10 is a schematic cross-sectional view of a sampling device according to the present invention incorporating a particle collector according to the present invention.

In FIG. 10, there is shown schematically the manner in which the collector is related to the separator within a sampling device according to the present invention.

In FIG. 10, the separator 12 is indicated diagrammatically only by three of the port constructions shown in FIG. 8. In reality, as described above, there will be thirty seven such ports, as described with reference to FIGS. 1 to 7, but for the purpose of explanation, only three are shown in FIG. 10.

Air which passes through the outlets provided by the curtain wall 30 of each port 20 is directed through the device to exhaust, and a convenient route for venting that air to exhaust is via exhaust passages at the periphery of the device, indicated schematically at 144 where the passages can be formed between the radially external surfaces of the cover 112/underfloor 60, spacer 110, partition 104, base section 106 and the side walls 108 of the device. Alternatively, the exhaust passages may be formed in the side walls 108 themselves. Or in any other convenient manner.

Thus, air which passes through the outlets can be vented, through the colonnades 64 from the collective outlets shown in FIG. 4, as shown by the arrows through exhaust ducts (not shown) to the exhaust passages 144.

The particles themselves which have been separated and have passed through the particle separator 12 are drawn, together with their accompanying air flow, towards the apertures 62 formed in the cover plate 112/underfloor 60. The particles are carried by the accompanying airflow into the plenum 114. With the removal of air through the exhaust passages 144, the quantity of air in the accompanying airflow is reduced to about 95% of the original intake of air by the device. The particles are moved in the accompanying airflow from the plenum 114 through the apertures 118 into the chamber 100. The momentum of the particles at the flow rate through the device causes the particles to be directed into the fluid film on the rotating wafer 122 while the accompanying air is drawn through the central apertures 124,120 respectively in the substrate 102 and supporting base section 106 to exhaust.

Alternatively to allowing the air to be exhausted, it is also foreseen that provision may be made for recycling the air back through the device. Means for so doing is not described but will be within the skill of the man skilled in the art.

Water or saline solution, with or without any additive by way of thickening agent is continually sprayed onto the area or region 132 (FIG. 12) of the wafer 122 to create a continuous film of such fluid over its surface. Particles that impact the fluid will be taken up by it and become trapped by the fluid. As the substrate rotates, it imparts a centrifugal force to the fluid causing it to move generally radially away from the axis of rotation of the substrate. As can be seen particularly from FIG. 12, the star shape of the aperture 130 in the wafer 126 provides sixteen edges 146 arranged in pairs, each leading to one of the channels 138, thus directing fluid flow towards the associated channel while the substrate rotates. Fluid carrying particles retained by the fluid is thus caused to flow along the channels 138 into the associated chambers 140 where the particles are collected for analysis.

Though not shown, means is also provided for draining off the carrier fluid and recycling to the aforementioned reservoir. Such means may be provided by a micropump or by channeling off the fluid under the effect of the centrifugal force acting on the fluid.

Figure 11:
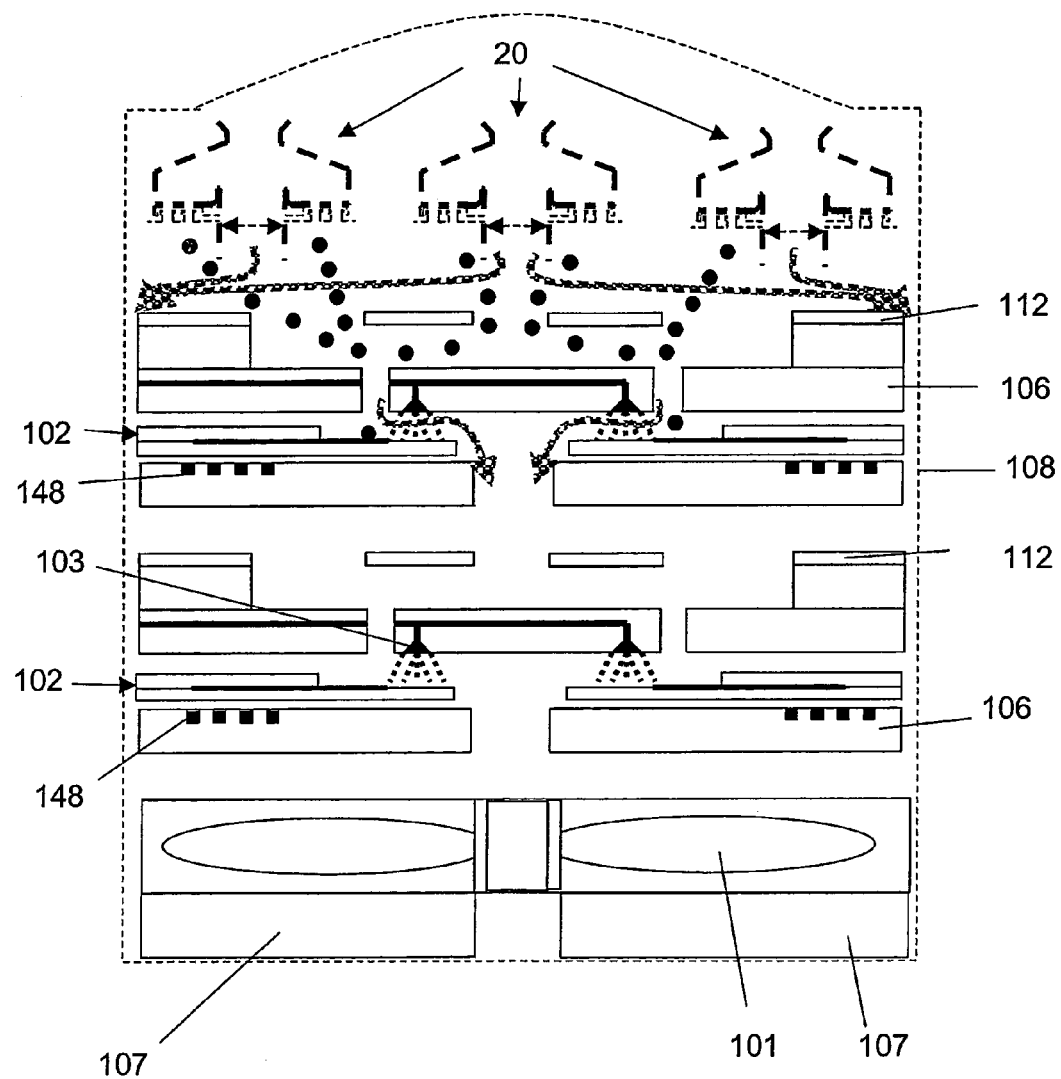
FIG. 11 is a schematic cross-sectional view of a sampling device according to the present invention incorporating a novel particle separator/collector according to the present invention.

Referring now to FIG. 11, there is illustrated therein a device similar to that of FIG. 10 but with a plurality of, i.e. two, rotatable substrates mounted therein. It will be readily understood from the following description that such a device can clearly incorporate more than two.

Such a device can itself operate not only as a particle collector but as a particle separator also. The separator ports 20 may be omitted and are therefore shown in dotted outline only, though for comprehensive separation and collection they are advantageously included. This embodiment of a device according to the present invention is hereinafter described purely by way of example and it is to be clearly understood that further embodiments and modifications are foreseen.

Each substrate stage is substantially identical to that described with reference to FIG. 10 and need not therefore be further described in detail. The arrangement of the device of FIG. 11 is such that any particles which are carried by air passing through the central apertures of the upper substrate stage are then drawn through the apertures 62 of the lower stage, and then through the further apertures 118 onto the lower substrate in the same manner as with the substrate unit shown in FIG. 10.

If the device shown in FIG. 11 is considered as a combined separator and collector, without the presence of the inlet ports 20, then it can be readily appreciated that the separation of particles from the air can be achieved by the upper and lower stages of the device.

In both of the embodiments shown in FIGS. 10 and 11, the or each base section 106 is provided with an array of sensors 148 adjacent each of the collection chambers 140. Such sensors can be of a conventional type for sensing the presence of any specie of micro-organisms such as bacteria, viruses, pathogens and the like, including but not limited to e-coli, anthrax or other potentially lethal organisms. The sensors may be active in the sense that they can detect the presence of such micro-organisms independently, or passive in the sense that they can be activated by fluorescence detection means at the inlet of the device with the sensors then confirming the presence of such micro-organisms in the particles collected in the chambers 140. The sensors may alternatively be provided on the wafer itself.

Though not illustrated, a device according to the present invention may be provided with valve control for controlling the rate of flow of air through the device according to the particles that are required to be detected.

Additionally, provision can be made for the device to record data relating to the collected particles.

A device according to the present invention may be constructed so that the or each substrate can be readily removable from the device if required, either so that the collected particles may be examined and/or analysed or so that the substrate can be cleansed and substituted by a fresh substrate, or disposed off if that becomes necessary.

One of the principal advances of the present invention over the prior art is that by transferring particles from air into an inert liquid, damage to the particles can be avoided while at the same time disposing of unwanted air. Not only are the particles far less inclined to be subject to damage but, as they are entrained in or by a liquid medium, they 'stick' to the medium and are less likely to be lost.

It is considered to be of primary importance that the viability of the particles is preserved, in order to be able to identify or culture any micro-organic particle in any subsequent on-device steps. The provision of a fluid film such as a water film permits use of a lower velocity of impaction (between 2-15 meters per second) than has hitherto been used, as the particles need only touch the water film to be extracted from the air and thus do not collide with the hard wafer surfaces and become damaged. Extracted particles will then be transferred to detectors by the continual water film flow.

The present invention also provides the advantage of removal of air. The particles of interest are extracted whilst the air (and any remaining smaller particles) is exhausted. The particles, as described above, are impacted against the fluid film, whilst the air is sucked out through the centre of the disc.

The sensors 148 may be above, below and on the or any substrate 102 and any type of suitable sensor could be incorporated. This includes for example optical sensors that detect particles in air prior to their impaction. It is foreseen that certain areas of the wafer, if formed as a CD, most probably a region near the middle, may also be used like a commercial CD-R to record data from the sensors.

In a further embodiment of the present invention, the or one of the substrates as the case may be may provide the core of a motor that is provided for rotating the or each substrate with the motor coil provided around that substrate and set into the outer walls of the device.

The invention claimed is:

1. A particle collector for collecting particles of a discrete particle mass/size separated from a flow of an ambient fluid medium, the collector comprising a chamber having mounted therein a substrate which is rotatable about an axis and onto which separated particles can be directed, the substrate having thereon a plurality of circumferentially-spaced channels each extending in a direction away from said axis and leading to a plurality of chambers in which the particles can be collected while the substrate is rotating, the collector further comprising means for depositing a fluid onto the substrate to form a film of said fluid at least in a region of the substrate onto which particles are directed during operation of the collector, the construction and arrangement of the collector being such that, as particles are deposited in the fluid, the fluid is caused to bear said particles to flow into the plurality of channels for deposition of the particles in the plurality of chambers.

2. A particle collector according to claim 1 wherein the substrate comprises a rotatable wafer.

3. A particle collector according to claim 1 wherein a central aperture is formed in the substrate to permit egress of the ambient fluid medium from which said particles have been separated.

4. A particle collector according to claim 3 wherein the region of the substrate forms an annulus around said aperture formed in the substrate.

5. A particle collector according to claim 1 wherein the channels and the chambers are formed radially outwardly of the region.

6. A particle collector according to claim 1 wherein the channels are arranged radially of the axis of rotation of the substrate.

7. A particle collector according to claim 1 wherein the channels and chambers are provided by a layer of material which is bonded to the substrate.

8. A particle collector according to claim 1 wherein the means for depositing a fluid onto the substrate comprises a plurality of spray nozzles arranged above the substrate.

9. A particle collector according to claim 1 wherein the fluid deposited onto the substrate is purified water.

10. A particle collector according to claim 1 wherein the fluid deposited onto the substrate is a saline solution.

11. A particle collector according to claim 1 wherein a reservoir is provided for storing a quantity of fluid for deposition onto the substrate.

12. A particle collector according to claim 11 wherein means is provided for recycling said quantity of fluid.

13. A particle collector according to claim 1 wherein the substrate is replaceable.

14. A particle collector according to claim 1 wherein a fan is employed for causing the flow of the ambient fluid medium to enable said particles and said ambient fluid medium to be drawn into the collector.

15. A particle collector according to claim 14 and comprising a motor for rotating the substrate and the fan.

16. A particle collector according to claim 1 wherein sensor means is provided adjacent each chamber for sensing the presence of a particle of any selected specie.

17. A particle collector according to claim 16 wherein means is provided for recording parameters associated with any selected particle that is sensed by any sensor means.

18. A particle collector according to claim 1 wherein the chamber has a ceiling and the means for depositing fluid onto the substrate is mounted in or on the ceiling above said region of the substrate, the ceiling further providing apertures for permitting ingress of said particles into the chamber.

19. A particle collector according to claim 1 wherein the substrate is made of silicon dioxide.

20. A particle collector according to claim 1 and comprising a second chamber having mounted therein a second substrate which is rotatable about said axis, the second chamber being located beneath said, first, said first chamber with access between the first and second chambers being provided whereby any particles uncollected in the first chamber can pass into the second chamber for collection on the second substrate, substrate having thereon a plurality of circumferentially-spaced channels each extending in a direction away from said axis and leading to a plurality of chambers in which the particles can be collected while the first and second substrates are rotating, the second chamber being provided with second means for depositing fluid onto the second substrate to form a film of said fluid at least in a region of the second substrate onto which particles are directed during operation of the collector.

21. A particle separator/collector for separating particles of a discrete particle size/mass from a flow of an ambient fluid medium, such as ambient air, and for collecting the separated particles, the separator/collector comprising a plurality of superimposed chambers each having mounted therein a substrate which is rotatable about an axis and onto which particles can be directed from the flow of ambient fluid medium, each substrate having thereon a plurality of circumferentially-spaced channels each extending in a direction away from said axis and leading to a plurality of chambers in which the particles can be collected while the substrate is rotating, the collector further comprising means for depositing a liquid onto each substrate to form a film of said liquid at least in a region of the substrate onto which particles are directed during operation of the separator/collector, the construction and arrangement of the separator/collector being such that, as particles are deposited in the liquid, the liquid is caused to bear said particles to flow into the plurality of channels for deposition of the particles in the plurality of chambers, and means for causing the ambient fluid medium to flow through the plurality of chambers to exhaust.

22. A particle collecting and sampling device, comprising;
a separator for separating particles of first and second mass/size ranges from an ambient fluid medium in which they are present, particles of the first range being of generally larger size/mass than particles of the second range, the separator comprising a body having an inlet provided by a plurality of inlet ports through which the ambient fluid medium can be admitted into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator; a particle collector comprising a chamber having mounted therein a substrate which is rotatable about an axis and onto which separated particles can be directed, the substrate having thereon a plurality of circumferentially-spaced channels each extending in a direction away from said axis and leading to a plurality of chambers in which the particles can be collected while the substrate is rotating, the collector further comprising means for depositing a fluid onto the substrate to form a film of said fluid at least in a region of the substrate onto which particles are directed during operation of the collector, the construction and arrangement of the collector being such that, as particles are deposited in the fluid, the fluid is caused to bear said particles to flow into the plurality of channels for deposition of the particles in the plurality of chambers and means for propelling air through the separator to the collector for collection thereby.

23. A particle collecting and sampling device comprising a separator for separating particles of first and second mass/size ranges from an ambient gaseous medium in which they are present, particles of the first range being of generally larger size/mass than particles of the second range, the separator comprising a body having an axis and an axial inlet provided by a plurality of inlet ports through which the gaseous medium can be drawn into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator; a particle collector comprising a chamber having mounted therein a substrate which is rotatable about an axis and onto which separated particles can be directed, the substrate having thereon a plurality of circumferentially-spaced channels each extending in a direction away from said axis and leading to a plurality of chambers in which the particles can be collected while the substrate is rotating, the collector further comprising means for depositing a fluid onto the substrate to form a film of said fluid at least in a region of the substrate onto which particles are directed during operation of the collector, the construction and arrangement of the collector being such that, as particles are deposited in the fluid, the fluid is caused to bear said particles to flow into the plurality of channels for deposition of the particles in the plurality of chambers and means for propelling air through the separator to the collector for collection thereby.

24. A particle collecting and sampling device according to claim 22 wherein the ports of the plurality of inlet ports are of substantially similar size and shape and are arranged concentrically with a substantially common orientation.

25. A particle collecting and sampling device according to claim 22 as appended thereto wherein each chamber has an axis parallel to the axis of the container and the outlet ports around the periphery of each chamber are arranged in concentric arrays about the respective chamber axis.

26. A particle collecting and sampling device according to claim 25 wherein the concentric arrays of outlet ports are arranged in an annular gallery above a floor area of the respective chamber.

27. A particle collecting and sampling device according to claim 26 wherein each of the outlet ports is provided by a passageway leading to an annular space formed beneath the gallery, the annular space being isolated from the chamber.

28. A particle collecting and sampling device according to claim 27 wherein one or more ducts leads from the annular space and is/are arranged for alignment and connection with a particle collector when the separator is connected thereto.

29. A particle collecting and sampling device according to claim 28 wherein a second annular space is provided beneath said annular space, and said second annular space is connected to said annular space whereby particles can pass from said annular space to said second annular space, said second annular space having outlets therefrom whereby said particles can be directed to said particle collector when the separator is connected thereto.

30. A particle collecting and sampling device according to claim 22 wherein the particles of said second range include particles of discrete third and fourth size/mass ranges where particles of the third range are of greater size/mass than the fourth range, the separator being capable of extracting particles of the fourth range in said annular space and particles of the third range proceeding to the second annular space.

31. A particle collecting and sampling device according to claim 29 wherein a plurality of annular spaces is provided beneath said second annular space, each annular space of said plurality thereof being connected to an immediately upper annular space whereby particles can pass from said immediately upper annular space thereto, and each annular space having outlets therefrom whereby said particles can be directed to said particle collector when the separator is connected thereto.

32. A particle collecting and sampling device according to claim 31 wherein each of the inlet ports has a floor and a lowermost one of said plurality of annular spaces is connected with an aperture leading to an outlet beneath said floor.

33. A particle collecting and sampling device according to claim 29 as appended thereto wherein the particles of the fourth range can be separated from particles of the third range is provided by separating said annular space into a first annular space and a second annular space with a partition therebetween such that the second annular space is separated from the outlet ports by the first annular space, the first annular space having an exit which is transverse to the axis of the respective chamber and through which particles of the fourth range can be drawn for collection, while the particles of the third range are directed through further outlets for separate collection.

34. A particle collecting and sampling device according to claim 22 which is portable.

35. A method of separating and collecting particles present in a fluid medium, the method comprising directing the fluid medium into a device comprising a chamber in which is rotatably mounted a substrate, directing a liquid onto the substrate to establish a liquid film thereon, the fluid medium being directed into the chamber at a rate such that the fluid medium can be removed from the chamber while permitting the particles therein to impact the liquid film, and drawing off the liquid having the particles embedded therein to collecting locations on the substrate.

36. A method according to claim 35 wherein the fluid medium is a gaseous medium, notably air.

37. A method according to claim 35 wherein the particles to be collected comprise micro-organisms.

38. A method according to claim 35 wherein particles entrained in the fluid medium are separated according to particle size/mass.

39. A method according to claim 35 wherein particles to be detected are in the size range of 2-20 microns.

40. A method according to claim 35 carried out using a particle collecting and sampling device which includes a particle collector for collecting particles of a discrete particle mass/size separated from a flow of an ambient fluid medium, the collector comprising a chamber having mounted therein a substrate which is rotatable about an axis and onto which separated particles can be directed, the substrate having thereon a plurality of circumferentially-spaced channels each extending in a direction away from said axis and leading to a plurality of chambers in which the particles can be collected while the substrate is rotating, the collector further comprising means for depositing a fluid onto the substrate to form a film of said fluid at least in a region of the substrate onto which particles are directed during operation of the collector, the construction and arrangement of the collector being such that, as particles are deposited in the fluid, the fluid is caused to bear said particles to flow into the plurality of channels for deposition of the particles in the plurality of chambers.

\* \* \* \* \*

UNITED STATES PATENT AND TRADEMARK OFFICE
CERTIFICATE OF CORRECTION

PATENT NO. : 7,458,287 B2
APPLICATION NO. : 11/547654
DATED : December 2, 2008
INVENTOR(S) : Alexander Roy Parfitt et al.

It is certified that error appears in the above-identified patent and that said Letters Patent is hereby corrected as shown below:

On the Title Page,
Please correct Assignee name, as follows: --(73) Assignee: BAE Systems plc. London (GB)--

Signed and Sealed this

Third Day of March, 2009

JOHN DOLL
*Acting Director of the United States Patent and Trademark Office*